United States Patent
Kurachi et al.

(10) Patent No.: US 9,277,869 B2
(45) Date of Patent: Mar. 8, 2016

(54) THIN-FILM PIEZOELECTRIC ELEMENT, THIN-FILM PIEZOELECTRIC ACTUATOR, THIN-FILM PIEZOELECTRIC SENSOR, HARD DISK DRIVE, AND INKJET PRINTER APPARATUS

(71) Applicant: TDK CORPORATION, Tokyo (JP)

(72) Inventors: Katsuyuki Kurachi, Tokyo (JP); Yasuhiro Aida, Tokyo (JP); Hitoshi Sakuma, Tokyo (JP); Kazuhiko Maejima, Tokyo (JP)

(73) Assignee: TDK CORPORATION, Tokyo (JP)

( * ) Notice: Subject to any disclaimer, the term of this patent is extended or adjusted under 35 U.S.C. 154(b) by 348 days.

(21) Appl. No.: 14/047,649

(22) Filed: Oct. 7, 2013

(65) Prior Publication Data
US 2014/0145555 A1    May 29, 2014

Related U.S. Application Data

(63) Continuation-in-part of application No. 13/687,786, filed on Nov. 28, 2012, now abandoned.

(51) Int. Cl.
| | | |
|---|---|---|
| H01L 41/187 | (2006.01) | |
| A61B 5/024 | (2006.01) | |
| B41J 2/14 | (2006.01) | |
| G01C 19/5621 | (2012.01) | |
| G01L 9/00 | (2006.01) | |
| G11B 5/55 | (2006.01) | |
| H01L 41/08 | (2006.01) | |
| H01L 41/316 | (2013.01) | |

(52) U.S. Cl.
CPC .......... *A61B 5/02444* (2013.01); *B41J 2/14233* (2013.01); *G01C 19/5621* (2013.01); *G01L 9/008* (2013.01); *G11B 5/483* (2015.09); *G11B 5/5552* (2013.01); *H01L 41/0815* (2013.01); *H01L 41/1873* (2013.01); *H01L 41/316* (2013.01); *B41J 2202/03* (2013.01)

(58) Field of Classification Search
CPC .... H01L 41/18; H01L 41/187; H01L 41/1873
USPC .................. 310/358; 252/62.9 R, 62.9 PZ
See application file for complete search history.

(56) References Cited

U.S. PATENT DOCUMENTS

| | | | |
|---|---|---|---|
| 2011/0121690 A1 | 5/2011 | Shibata et al. | |
| 2014/0049138 A1* | 2/2014 | Shiraki | H01L 41/1873 310/330 |

FOREIGN PATENT DOCUMENTS

| | | |
|---|---|---|
| JP | A-2011-109037 | 6/2011 |
| JP | A-2011-204887 | 10/2011 |

* cited by examiner

*Primary Examiner* — Derek Rosenau
(74) *Attorney, Agent, or Firm* — Oliff PLC

(57) ABSTRACT

There are provided a thin-film piezoelectric element including a piezoelectric thin film which has an alkali niobate-based perovskite structure represented by the composition formula $(K_{1-w-x}Na_wSr_x)_m(Nb_{1-y}Zr_y)O_3$ and which is preferentially oriented to (001), and a pair of electrode films that sandwich the piezoelectric thin film, a thin-film piezoelectric actuator, and a thin-film piezoelectric sensor each including the thin-film piezoelectric element.

11 Claims, 9 Drawing Sheets

THIN-FILM PIEZOELECTRIC ELEMENT, THIN-FILM PIEZOELECTRIC ACTUATOR, THIN-FILM PIEZOELECTRIC SENSOR, HARD DISK DRIVE, AND INKJET PRINTER APPARATUS

This is a Continuation-in-Part of application Ser. No. 13/687,786 filed Nov. 28, 2012. The disclosure of the prior application is hereby incorporated by reference herein in its entirety.

BACKGROUND OF THE INVENTION

1. Field of the Invention

The present invention relates to a thin-film piezoelectric element composed of a thin-film piezoelectric material; a thin-film piezoelectric actuator and a thin-film piezoelectric sensor that include the thin-film piezoelectric elements; and a hard disk drive and an ink jet printer apparatus that include the thin-film piezoelectric actuators.

2. Related Background Art

In recent years, there have been advances in practical use of thin-film piezoelectric elements including thin-film piezoelectric materials, instead of bulk piezoelectric materials. Examples thereof include gyroscope sensors, pressure sensors, pulse wave sensors, shock sensors, and microphones, which use a piezoelectric effect, in which a force applied to a piezoelectric film is converted into a voltage; and actuators, ink jet heads, speakers, beepers, and resonators, which use an inverse piezoelectric effect, in which the application of a voltage to a piezoelectric film produces a distortion of the piezoelectric film.

A reduction in the thickness of piezoelectric materials enables the miniaturization of elements and widens the field of application. Furthermore, many elements can be collectively produced on a substrate, thereby increasing the mass productivity. There are many advantages in performance, for example, improvement in sensitivity as a sensor.

In piezoelectric elements, high dielectric loss of piezoelectric materials often causes heat generation and so forth during operation, which is a problem of reliability. In thin-film piezoelectric materials, a material having low dielectric loss comparable to bulk piezoelectric materials are not found. Thus, the design of a piezoelectric thin film having low dielectric loss is an important subject.

Lead zirconate titanate (PZT) is well known as an excellent piezoelectric material. Since it contains lead, alternative (lead-free) materials have been studied in view of the environment and the human body. However, an alternative material having piezoelectric properties comparable to PZT is not found.

PRIOR ART LITERATURE

Patent Literature

[PTL 1] Japanese Unexamined Patent Application Publication No. 2011-204887
[PTL 2] Japanese Unexamined Patent Application Publication No. 2011-109037

SUMMARY OF INVENTION

One of the important factors for piezoelectric properties is dielectric loss. An electric field applied to a piezoelectric material is partially consumed as thermal energy by the presence of dielectric loss. In general, in a piezoelectric material, the following equation holds: $D = \epsilon \cdot \epsilon_0 \cdot E$ (where D represents a electric flux density, E represents an electric field, $\epsilon$ represents a dielectric constant, and $\epsilon_0$ represents the dielectric constant of vacuum). When the electric field E is an alternating current, the dielectric constant $\epsilon$ is a real number if no dielectric loss is present. If the dielectric loss is present, a complex number $= \epsilon' - j \cdot \epsilon''$, where the real part $\epsilon'$ is usually referred to as permittivity, and the imaginary part $\epsilon''$ corresponds to the dielectric loss. $\tan \delta = \epsilon''/\epsilon'$ is referred to as "dielectric loss tangent", where $\delta$ is referred to as a "loss angle". Dielectric loss is caused by the fact that the electric flux density D of a dielectric material cannot immediately follow the electric field E and that the phase of D is delayed from the phase of E by $\delta$. A lower dielectric loss of a dielectric material is more preferred.

As a method for reducing the dielectric loss, there is a method in which carbon and hydrogen are incorporated into a piezoelectric material (PTL 1). However, conditions, such as a deposition temperature, are required to be precisely controlled. When a deposition apparatus is subjected to maintenance, the conditions are often required to be revised.

As a method for improving piezoelectric properties D31, there is a method in which a piezoelectric material is allowed to have a composition shifted from a stoichiometric composition (PTL 2). However, this material has high dielectric loss, so the material cannot provide the piezoelectric performance, depending on a frequency used.

The present invention has accomplished in consideration of the foregoing problems in the conventional art. It is an object of the present invention to provide a thin-film piezoelectric element having a larger amount of displacement, the thin-film piezoelectric element including a piezoelectric thin film composed of a lead-free piezoelectric material with reduced dielectric loss.

To achieve the foregoing object, a thin-film piezoelectric element according to the present invention includes:
a piezoelectric thin film; and a pair of electrode films that sandwich the piezoelectric thin film,
in which the piezoelectric thin film has an alkali niobate-based perovskite structure represented by the composition formula $(K_{1-w-x}Na_wSr_x)_m(Nb_{1-y}Zr_y)O_3$ and is preferentially oriented to (001),
wherein $0.95 \leq m < 1.05$, and $0.6 \leq (m \cdot x/y) \leq 0.8$.

When m is less than 0.95, the dielectric loss cannot be reduced. When m is 1.05 or more, it is impossible to prevent the dielectric loss from increasing.

When m·x/y is less than 0.6, the dielectric loss cannot be sufficiently reduced in the vicinity of the stoichiometric composition, i.e., when m is close to 1. When m·x/y exceeds 0.8, it is impossible to prevent the dielectric loss from increasing in the vicinity of the stoichiometric composition. In the case where these two composition regions are satisfied, sufficiently low dielectric loss is achieved.

The piezoelectric thin film used in the thin-film piezoelectric element has a composition in the vicinity of the stoichiometric composition. Thus, a lattice defect is less likely to be formed in the perovskite structure, thereby providing more stable piezoelectric, dielectric properties.

The piezoelectric thin film has a perovskite structure and is preferentially oriented to (001). This results in the suppression of the dielectric loss of the thin-film piezoelectric element and an improvement in piezoelectric properties. In the case where the piezoelectric thin film is preferentially oriented to a direction other than (001), it is impossible to reduce the dielectric loss or achieve sufficient piezoelectric properties.

Here, "preferentially orientated" indicates that the proportion of the intensity of a signal of a main orientation obtained by X-ray diffraction measurement, i.e., a signal having the highest intensity, to the total peak intensity is 50% or more. The degree of (001) orientation indicates the peak intensity of (001)/total peak intensity and is expressed in units of (%).

With respect to the composition of the piezoelectric thin film, a Na (sodium)/(Na+K (potassium)) ratio may be 0.5 or more and 0.75 or less. A Na/(Na+K) ratio of 0.5 or more results in a further reduction in leakage current density when a voltage is applied to the electrode films. A Na/(Na+K) ratio of 0.75 or less results in further improvement in piezoelectric properties.

The piezoelectric element with a leakage current density of $1 \times 10^{-5}$ A/cm$^2$ or less is practical. The piezoelectric element preferably has a leakage current density of $1 \times 10^{-7}$ A/cm$^2$ or less.

The thin-film piezoelectric element according to the present invention may include a strontium ruthenate thin film provided between the piezoelectric thin film and at least one of the pair of electrode films. In the case where the strontium ruthenate thin film is used as an intermediate film and is formed before the formation of the piezoelectric thin film, the piezoelectric thin film is easily preferentially oriented to (001).

A thin-film piezoelectric actuator according to the present invention includes the thin-film piezoelectric element which has the alkali niobate-based perovskite structure represented by the composition formula described above and which is preferentially oriented to (001). Specific examples of the thin-film piezoelectric actuator include head assemblies of hard disk drives and piezoelectric actuators of ink jet printer heads.

A thin-film piezoelectric sensor according to the present invention includes the thin-film piezoelectric element which has the alkali niobate-based perovskite structure represented by the composition formula described above and which is preferentially oriented to (001). Specific examples of the thin-film piezoelectric sensor include gyroscope sensors, pressure sensors, and pulse wave sensors.

A hard disk drive and an ink jet printer apparatus according to the present invention each include the thin-film piezoelectric actuator.

The thin-film piezoelectric element according to the present invention has lower dielectric loss than conventional thin-film piezoelectric elements. Thus, in the thin-film piezoelectric element, the thin-film piezoelectric actuator, the thin-film piezoelectric sensor, the hard disk drive, and the ink jet printer apparatus according to the present invention, operation failure is not caused by heat generation during operation, thereby improving reliability.

The thin-film piezoelectric element according to the present invention has low dielectric loss in a high frequency region and can be applied to a high-frequency element.

The piezoelectric thin film according to the present invention is a lead-free piezoelectric material, thus reducing the effect on the environment and the human body. Hence, the thin-film piezoelectric element, the thin-film piezoelectric actuator, the thin-film piezoelectric sensor, the hard disk drive, and the ink jet printer apparatus according to the present invention can be applied to applications where the use of conventional thin-film piezoelectric elements is difficult.

DESCRIPTION OF EMBODIMENTS

Figure 1:
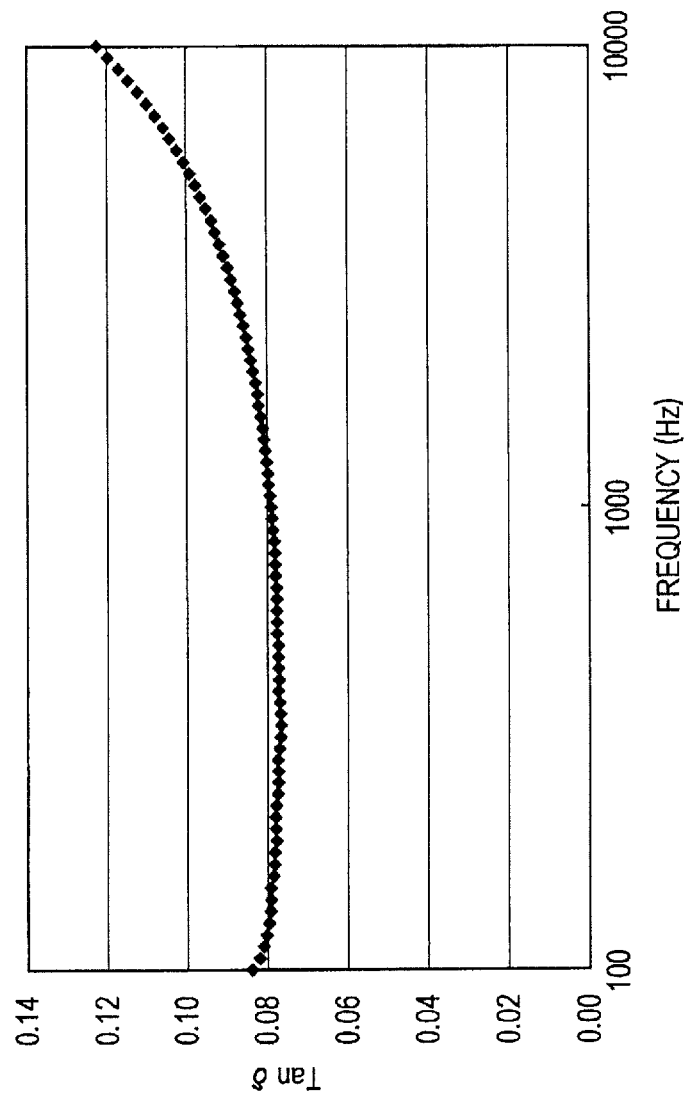
FIG. 1 is a correlation graph illustrating the relationship between Tan δ of a conventional lead-free piezoelectric thin film and the measurement frequency.

A preferred embodiment of the present invention will be described in detail below with reference to the drawings. In the drawings, the same or equivalent elements are designated using the same reference numerals. The positional relationship of the top, bottom, left, and right is as illustrated in the drawings. Furthermore, redundant descriptions are not repeated.

(Thin-Film Piezoelectric Element)

FIG. 1 is a correlation graph illustrating the relationship between the dielectric loss tangent Tan δ of a conventional lead-free piezoelectric thin film and the measurement frequency. The graph demonstrates that Tan δ increases with increasing frequency.

Figure 2:
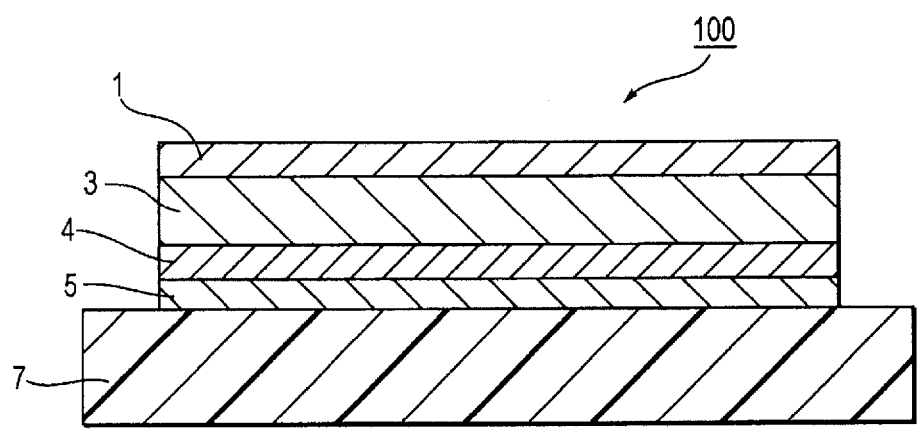
FIG. 2 is a structural drawing of a thin-film piezoelectric element according to the present invention.

FIG. 2 illustrates a thin-film piezoelectric element 100 according to this embodiment. The thin-film piezoelectric element 100 includes a substrate 7, a first electrode film 5 provided on the substrate 7, an intermediate film 4 provided on the first electrode film 5, a piezoelectric thin film 3 provided on the intermediate film 4, and a second electrode film 1 provided on the piezoelectric thin film 3.

As the substrate 7, for example, a silicon (100) substrate may be used. The substrate 7 has a thickness of, for example, 100 μm or more and 1000 μm or less. As the substrate 7, a silicon substrate having a silicon substrate having a surface different from the (100) surface, a silicon on insulator (SOI) substrate, a silica glass substrate, a compound semiconductor substrate composed of, for example, GaAs, a sapphire substrate, a metal substrate composed of, for example, stainless steel, a MgO substrate, or a SrTiO$_3$ substrate may also be used.

The first electrode film 5 is composed of, for example, platinum (Pt). The first electrode film 5 preferably has a thickness of 0.02 μm or more and 1.0 μm or less. A thickness of less than 0.02 μm results in an insufficient function as an electrode. A thickness of more than 1.0 μm disadvantageously inhibits the displacement characteristics of the piezoelectric material. When a Pt film is formed by a sputtering method on the silicon (100) substrate heated to about 400° C. to about 500° C., the Pt film is a (100)-oriented film having a high degree of orientation. The piezoelectric thin film 3 subsequently formed can also be the piezoelectric thin film 3 having a high degree of orientation.

The piezoelectric thin film 3 is composed of a potassium sodium niobate (hereinafter, also referred to as "KNN"), which is a potassium sodium niobate compound having a composition of $(K_{1-w-x}Na_wSr_x)_m(Nb_{1-y}Zr_y)O_3$, where m is in the range given by formula (1), and m·x/y corresponding to the composition ratio Sr/Zr is in the range given by formula (2):

$$0.95 \leq m < 1.05 \quad \text{formula (1)}$$

$$0.6 \leq (m \cdot x/y) \leq 0.8 \quad \text{formula (2)}$$

In the case where these two composition ranges are satisfied, sufficiently low dielectric loss is achieved. To improve the Curie point, reduce the leakage current density, and so forth, elements, such as Ta (tantalum), Li (lithium), Ba (barium), and Mn (manganese), may also be added. The thickness of the piezoelectric thin film 3 is not particularly limited and may be, for example, about 0.5 to about 5 µm.

The piezoelectric thin film 3 is formed by a sputtering method or an evaporation method while the substrate 7 on which the first electrode film 5 is formed is heated to about 400° C. to about 500° C.

In the piezoelectric thin film 3, the ratio Na/(Na+K) may be 0.5 or more and 0.75 or less. A ratio of 0.5 or more reduces the leakage current density. A ratio of 0.75 or less improves the piezoelectric properties.

The piezoelectric thin film 3 may contain a small amount of an element or compound other than the foregoing composition as long as the structure and properties thereof are not significantly affected.

The piezoelectric thin film 3 preferably has a dielectric loss tangent Tan $\delta_{100}$ of 0.05 or less at a measurement frequency of 100 Hz. Thus, problems, such as heat generation, during the operation of the piezoelectric thin film 3 do not arise.

Needless to say, a lower dielectric loss tangent Tan $\delta_{100}$ is more preferred. The actually possible lower limit is about 0.01.

In the piezoelectric thin film 3, the ratio of the dielectric loss tangent Tan $\delta_{10000}$ at a measurement frequency of 10 KHz to the dielectric loss tangent Tan $\delta_{100}$ at a measurement frequency of 100 Hz, i.e., Tan $\delta_{10000}$/Tan $\delta_{100}$, is preferably 1.5 or less. In this case, the thin-film piezoelectric element can be used at high frequencies.

Typically, the dielectric loss tangent increases as the measurement frequency increases. Thus, the value of Tan $\delta_{10000}$/Tan $\delta_{100}$ is usually 1.0 or more.

The second electrode film 1 is composed of, for example, platinum (Pt). The second electrode film 1 has a thickness of, for example, 0.02 µM or more and 1.0 µM or less. As with the first electrode film 5, the second electrode film 1 is formed by a sputtering method.

As illustrated in FIG. 2, the intermediate film 4 may be provided between the first electrode film 5 and the piezoelectric thin film 3. The intermediate film 4 is preferably composed of strontium ruthenate $SrRuO_3$, which is a conductive oxide. In this case, the preferred orientation of the (001) plane of the piezoelectric thin film 3 is easily achieved, thereby resulting in improvements in piezoelectric properties and dielectric loss.

The intermediate film 4 desirably has a thickness of 0.01 µm or more and 0.1 µm or less. A thickness of 0.01 µm or more and 1 µm or less results in an increase in the crystallinity of the intermediate film 4, thus resulting in an increase in the crystallinity of the piezoelectric thin film 3. This enhances the effects of improving the piezoelectric properties and reducing the dielectric loss.

The thin-film piezoelectric element 100 may have a structure without the substrate 7. In the case of a device that requires the amount of displacement of the element, the removal of the substrate 7 increases the amount of displacement. Furthermore, various protective films may be formed on the thin-film piezoelectric element 100.

(Thin-Film Piezoelectric Actuator)

Figure 3A:
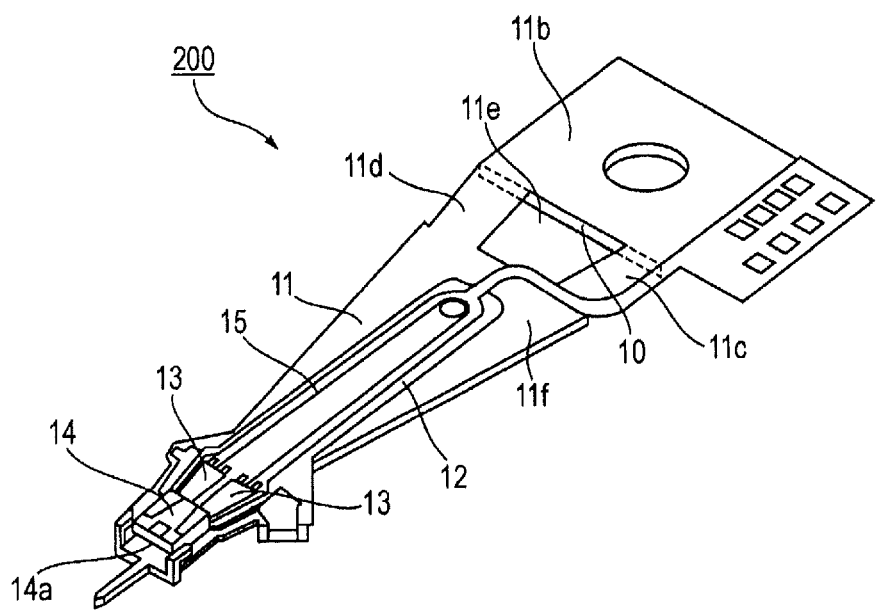
FIGS. 3A and 3B are structural drawings of thin-film piezoelectric actuators according to the present invention.

FIG. 3A is a structural drawing of a head assembly mounted on a hard disk drive serving as an example of a thin-film piezoelectric actuator including these thin-film piezoelectric elements. As illustrated in this figure, the head assembly 200 includes, as main components, a base plate 10; a load beam 11; a flexure 12; first and second thin-film piezoelectric elements 13 serving as driving elements; and a slider 14 provided with a head element 14a.

The load beam 11 includes a base end portion 11b fixed to the base plate 10 by, for example, beam welding; first and second plate springs 11c and 11d extending from the base end portion 11b in a tapered shape; an opening 11e formed between the first and second plate springs 11c and 11d; and a main beam portion 1 if which is continuous with the first and second plate springs 11c and 11d and which extends linearly in the tapered shape.

The first and second thin-film piezoelectric elements 13 are arranged on a flexible wiring board 15, which is part of the flexure 12, with a predetermined distance kept therebetween. The slider 14 is fixed to a tip of the flexure 12 and moves rotationally as the first and second thin-film piezoelectric elements 13 expand and contract.

Each of the first and second thin-film piezoelectric elements 13 includes a piezoelectric thin film and a pair of electrode films that sandwich the piezoelectric thin film. In the case where a low-dielectric-loss alkali niobate-based piezoelectric thin film according to the present invention is used as the piezoelectric thin film, it is possible to suppress heat generation during operation and achieve a sufficient amount of displacement.

Figure 3B:
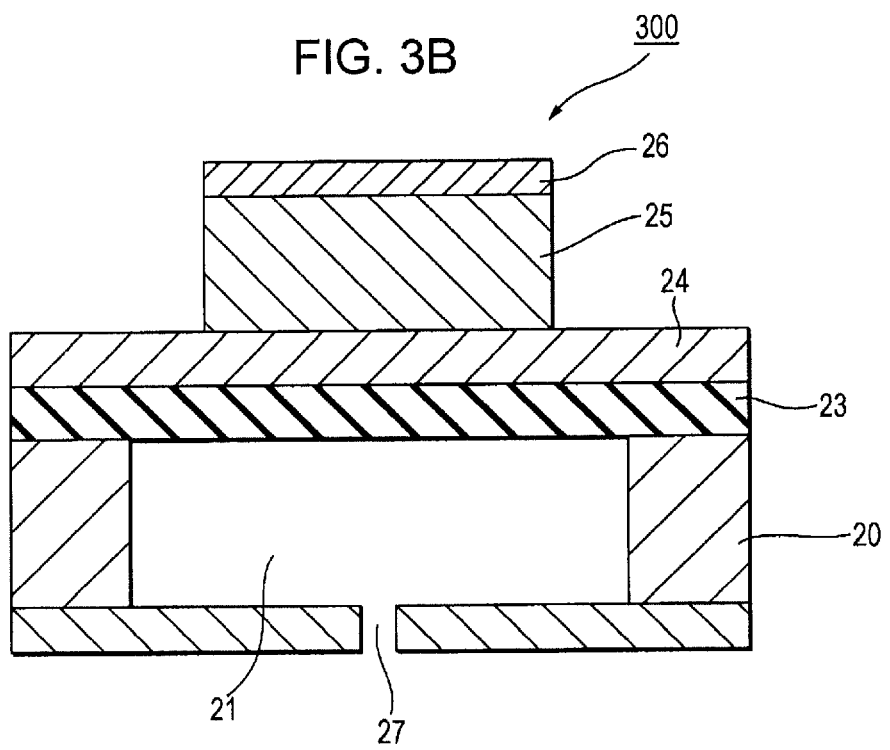

FIG. 3B is a structural drawing of a piezoelectric actuator of an ink jet printer head as another example of the thin-film piezoelectric actuator including the thin-film piezoelectric element.

A piezoelectric actuator 300 includes an insulating film 23, a lower electrode film 24, a piezoelectric thin film 25, and an upper electrode film 26 stacked on a substrate 20.

In the case where a predetermined ejection signal is not fed and where a voltage is not applied between the lower electrode film 24 and the upper electrode film 26, the piezoelectric thin film 25 is not deformed. A pressure in a pressure chamber 21 provided with a thin-film piezoelectric element to which an ejection signal is not fed is not changed, so that an ink droplet is not ejected from a nozzle 27.

In the case where a predetermined ejection signal is fed and where a fixed voltage is applied between the lower electrode film 24 and the upper electrode film 26, the piezoelectric thin film 25 is deformed. In the pressure chamber 21 provided with the thin-film piezoelectric element to which the ejection signal is fed, the insulating film 23 is largely bent. Thus, pressure in the pressure chamber 21 is instantaneously increased, thereby ejecting an ink droplet from the nozzle 27.

Here, in the case where a low-dielectric-loss alkali niobate-based piezoelectric thin film according to the present invention is used as the piezoelectric thin film, it is possible to suppress heat generation during operation and achieve a sufficient amount of displacement.

(Thin-Film Piezoelectric Sensor)

Figure 4A:
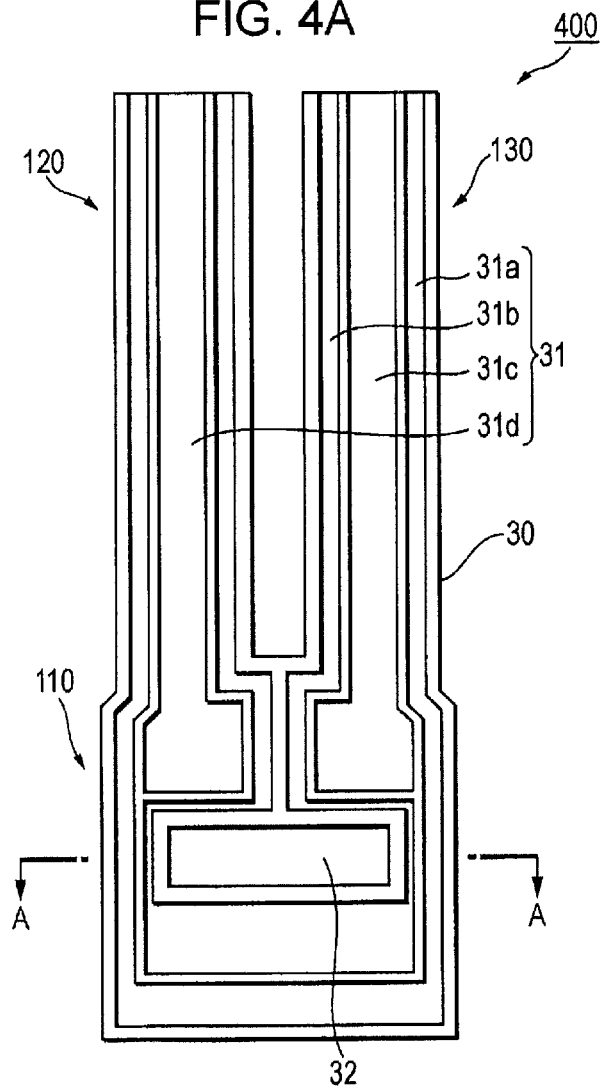
FIGS. 4A to 4D are structural drawings of thin-film piezoelectric sensors according to the present invention.
Figure 4B:
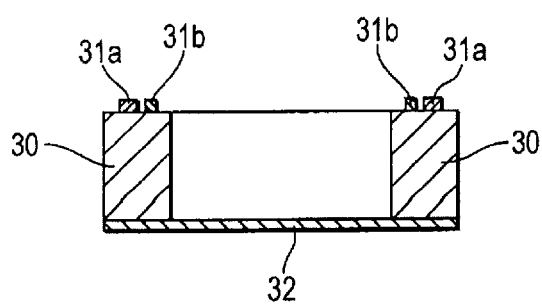

FIG. 4A is a structural drawing (plan view) of a gyroscope sensor as an example of a thin-film piezoelectric sensor including the thin-film piezoelectric element. FIG. 4B is a cross-sectional view taken along line A-A in FIG. 4A.

A gyroscope sensor 400 is a tuning fork-type angular velocity detecting element that includes a base portion 110 and two arms 120 and 130 connected to a surface of the base portion 110. The gyroscope sensor 400 is produced by microfabrication of a piezoelectric thin film 30, an upper electrode film 31, and a lower electrode film 32, which constitute the thin-film piezoelectric element, into the shape of a tuning fork-type resonator. The components (the base portion 110 and the arms 120 and 130) are integrally formed into a thin-film piezoelectric element.

Driving electrode films 31a and 31b and a detection electrode film 31d are formed on a first main surface of one arm 120. Similarly, the driving electrode films 31a and 31b and a detection electrode film 31c are formed on a first surface of the other arm 130. These electrode films 31a, 31b, 31c, and 31d are formed by etching the upper electrode film 31 into a predetermined electrode shape.

The lower electrode film 32 is entirely formed on a second main surface (a main surface opposite the first main surface) of each of the base portion 110 and the arms 120 and 130 and functions as a ground electrode of the gyroscope sensor 400.

Here, letting the longitudinal direction of each of the arms 120 and 130 be a Z direction, and letting a plane including the main surfaces of the two arms 120 and 130 be an XZ plane, a rectangular coordinate system XYZ is defined.

When a driving signal is fed to the driving electrode films 31a and 31b, the two arms 120 and 130 are excited in an in-plane vibration mode. The in-plane vibration mode refers to a vibration mode in which the two arms 120 and 130 vibrate in a direction parallel to the main surfaces of the two arms 120 and 130. For example, when the one arm 120 is excited in a −X direction at a velocity of V1, the other arm 130 is excited in a +X direction at a velocity of V2.

In the case where the gyroscope sensor 400 is rotated at angular velocity of around the Z-axis as the axis of rotation in this state, the Coriolis force acts on each of the arms 120 and 130 in a direction orthogonal to the direction of velocity, so that they start to be excited in an out-plane vibration mode. The out-plane vibration mode refers to a vibration mode in which the two arms 120 and 130 vibrate in a direction orthogonal to the main surfaces of the two arms 120 and 130. For example, when the Coriolis force F1 acts on the one arm 120 in a −Y direction, the Coriolis force F2 acts on the other arm 130 in a +Y direction.

The magnitude of the Coriolis forces F1 and F2 is proportional to the angular velocity ω. Thus, the mechanical strains of the arms 120 and 130 due to the Coriolis forces F1 and F2 are converted by the piezoelectric thin film 30 into electrical signals (detection signals). The electrical signals can be taken from the detection electrode films 31c and 31d to determine the angular velocity ω.

In the case where a low-dielectric-loss alkali niobate-based piezoelectric thin film according to the present invention is used as the piezoelectric thin film, it is possible to suppress heat generation during operation and achieve sufficient detection sensitivity.

Figure 4C:
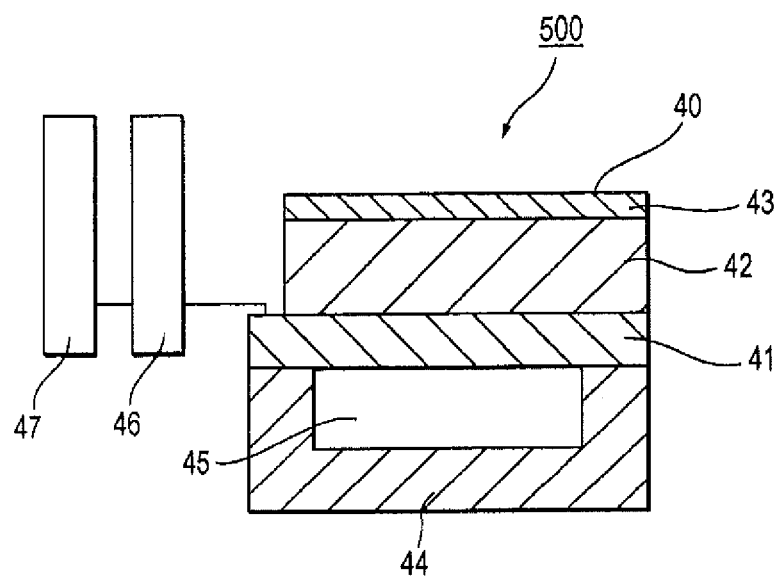

FIG. 4C is a structural drawing of a pressure sensor as a second example of the thin-film piezoelectric sensor including the thin-film piezoelectric element.

A pressure sensor 500 includes a cavity 45 configured to respond when subjected to pressure; a support 44 that supports a thin-film piezoelectric element 40; a current amplifier 46; and a voltage-measuring device 47. The thin-film piezoelectric element 40 includes a common electrode film 41, a piezoelectric thin film 42, and an individual electrode film 43 stacked, in that order, on the support 44. Here, when an external force is applied, the thin-film piezoelectric element 40 is bent, so that a voltage is detected by the voltage-measuring device 47.

In the case where a low-dielectric-loss alkali niobate-based piezoelectric thin film according to the present invention is used as the piezoelectric thin film, it is possible to suppress heat generation during operation and achieve sufficient detection sensitivity.

Figure 4D:
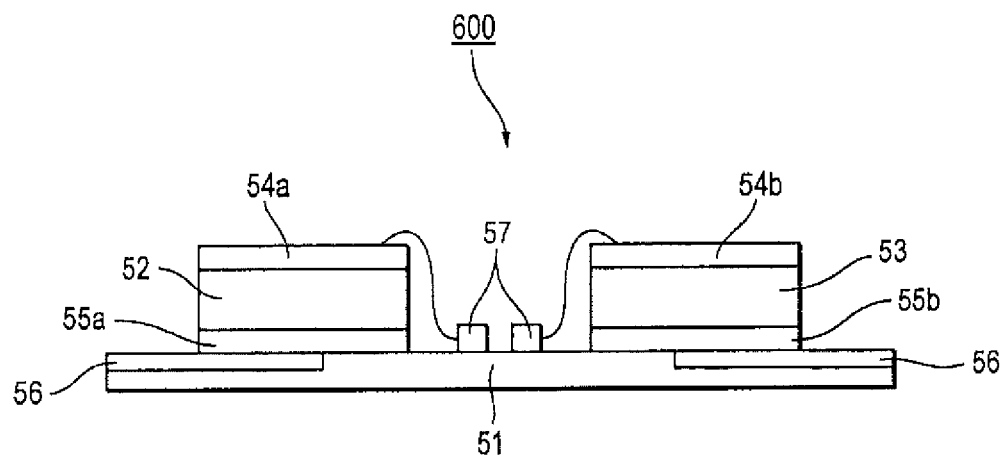

FIG. 4D is a structural view of a pulse wave sensor as a third example of the thin-film piezoelectric sensor including the thin-film piezoelectric element.

A pulse wave sensor 600 includes a transmission piezoelectric element and a receiving piezoelectric element mounted on a substrate 51. Here, in the transmission piezoelectric element, electrode films 54a and 55a are formed on surfaces of a transmission piezoelectric thin film 52 in the thickness direction. In the receiving piezoelectric element, electrode films 54b and 55b are formed on surfaces of a receiving piezoelectric thin film 53 in the thickness direction. Electrodes 56 and upper surface electrodes 57 are formed on the substrate 51. Each of the electrode films 54a and 54b is electrically connected to the respective upper surface electrodes 57 with a wire.

To detect the pulse wave of a living body, the back surface of the substrate of the pulse wave sensor 600 (a surface on which the piezoelectric element is not mounted) is brought into contact with the living body. A specific driving voltage signal is sent to the electrode films 54a and 55a of the transmission piezoelectric element at the time of detection of the pulse wave. The transmission piezoelectric element is excited in response to the driving voltage signal sent to the electrode films 54a and 55a to generate ultrasound and transmits the ultrasound into the living body. The ultrasound transmitted into the living body is reflected from a blood flow and received by the receiving piezoelectric element. The receiving piezoelectric element converts the received ultrasound into a voltage signal and sends the signal from the electrode films 54b and 55b.

In the case where a low-dielectric-loss alkali niobate-based piezoelectric thin film according to the present invention is used as the piezoelectric thin film, it is possible to suppress heat generation during operation and achieve sufficient detection sensitivity.

(Hard Disk Drive)

Figure 5:
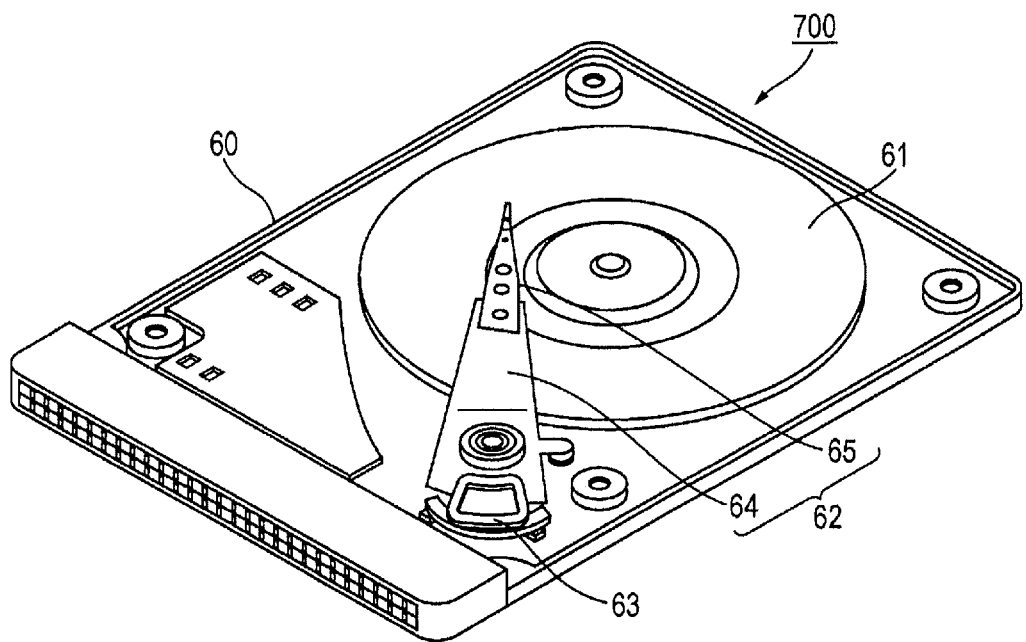
FIG. 5 is a structural drawing of a hard disk drive according to the present invention.

FIG. 5 is a structural view of a hard disk drive on which the head assembly illustrated in FIG. 3A is mounted.

A hard disk drive 700 is provided with a hard disk 61 as a recording medium and a head stack assembly 62 configured to record and reproduce magnetic information in a housing 60. The hard disk 61 is rotated by a motor that is not illustrated.

The head stack assembly 62 is a component in which a plurality of assemblies each including an actuator arm 64 pivotally supported around a pivot axis by a voice coil motor 63 and a head assembly 65 connected to the actuator arm 64 are stacked in the direction of depth. The slider 14 is attached to the tip of the head assembly 65 so as to face the hard desk 61 (see FIG. 3A).

For the head assembly 65, a method for moving the head element 14a (see FIG. 3A) in two modes is employed. A relatively large movement of the head element 14a is controlled by driving the whole of the head assembly 65 and the actuator arm 64 with the voice coil motor 63. A fine movement is controlled by driving the slider 14 at the tip of the head assembly 65.

With respect to the thin-film piezoelectric element used for the head assembly 65, in the case where a low-dielectric-loss alkali niobate-based piezoelectric thin film according to the present invention is used as the piezoelectric thin film, it is possible to suppress heat generation during operation and achieve a sufficient amount of displacement.

(Ink Jet Printer Apparatus)

Figure 6:
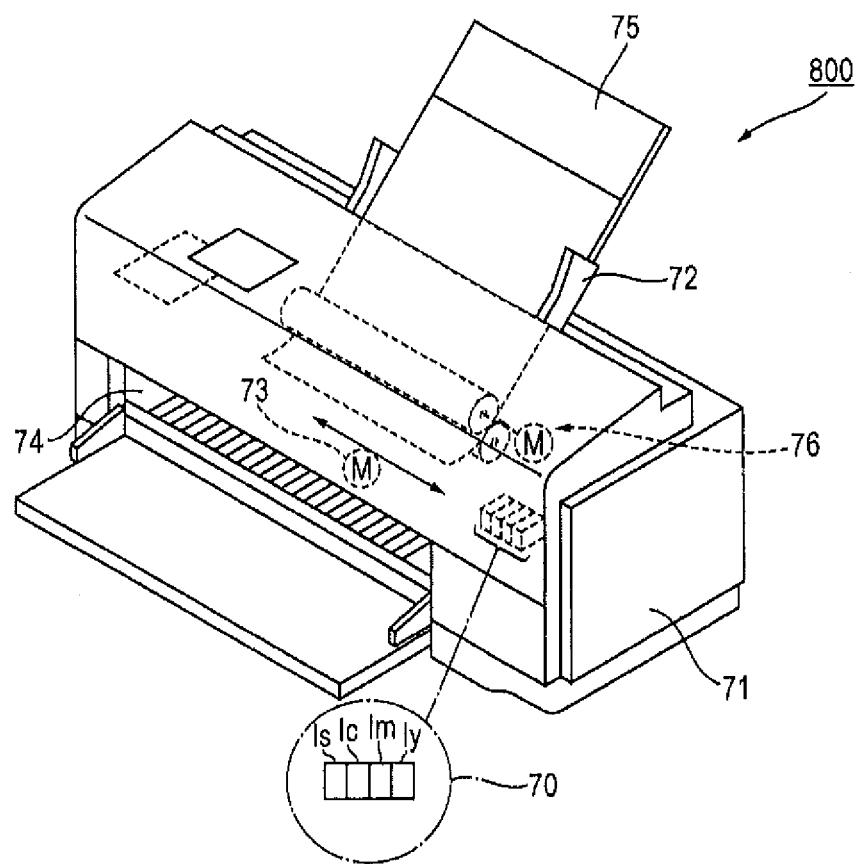
FIG. 6 is a structural drawing of an ink jet printer apparatus according to the present invention.

FIG. 6 is a structural view of an ink jet printer apparatus on which the ink jet printer head illustrated in FIG. 3B is mounted.

An ink jet printer apparatus 800 mainly includes an ink jet printer head 70, a main body 71, a tray 72, and a head-driving mechanism 73.

The ink jet printer apparatus 800 is provided with ink cartridges of a total of four colors, yellow, magenta, cyan, and black, and is configured to provide full-color printing. The ink jet printer apparatus 800 includes a special controller board and so forth therein. The controller board controls ink ejection timing from the ink jet printer head 70 and the scan of the head-driving mechanism 73. The main body 71 is provided with the tray 72 on a back panel and an automatic sheet feeder (automatic continuous document feeder mechanism) 76 therein. The automatic sheet feeder 76 automatically feeds recording paper 75 and delivers the recording paper 75 from a front outlet 74.

With respect to the thin-film piezoelectric element used for the piezoelectric actuator of the ink jet printer head 70, in the case where a low-dielectric-loss alkali niobate-based piezoelectric thin film according to the present invention is used as the piezoelectric thin film, it is possible to provide a high-safety ink jet printer apparatus with low heat generation during operation.

EXAMPLES

Thin-Film Piezoelectric Element

While the present invention will be more specifically described below on the basis of examples and comparative examples, the present invention is not limited to these examples described below.

Example 1

The thin-film piezoelectric element 100 according to Example 1 was produced as described below.

The silicon (100) substrate 7 was heated to 400° C. Pt was epitaxially grown by a sputtering method on the silicon substrate 7 to form a 200-nm-thick Pt film serving as the first electrode film 5 in such a manner that the Pt film was oriented to the plane of the silicon substrate 7. In this case, the deposition rate was 0.2 nm/sec.

Next, the silicon substrate 7 was heated to 550° C. The piezoelectric thin film 3 was epitaxially grown by a sputtering method so as to have a thickness of 2000 nm. In this case, a sintered compact having a composition of $(K_{0.17}Na_{0.76}Sr_{0.07})_{0.96}(Nb_{0.9}Zr_{0.1})O_3$ was used as a sputtering target for the piezoelectric thin film 3. The film composition of the piezoelectric thin film 3 was almost the same as the target composition.

Next, a Pt film having a thickness of 200 nm was formed as the second electrode film 1 by a sputtering method at room temperature.

Then the stack including the piezoelectric thin film 3 was patterned by photolithography and etched by RIE. The silicon substrate 7 was diced to form the thin-film piezoelectric element 100 having a size of 2 mm×20 mm.

Examples 2 to 9 and Comparative Examples 1 to 5

The thin-film piezoelectric elements 100 were produced as in Example 1, except that the piezoelectric thin films 3 were formed using sputtering targets containing materials described in Table 1 as sputtering targets for the piezoelectric thin films 3.

Examples 10 to 12

As with Example 1, each silicon substrate 7 was heated to 400° C. Pt was epitaxially grown by a sputtering method on the silicon substrate 7 to form a 200-nm-thick Pt film serving as the first electrode film 5 in such a manner that the Pt film was oriented to the plane of the silicon substrate 7. A 35-nm-thick strontium ruthenate $SrRuO_3$ film serving as the intermediate film 4 was formed by a sputtering method on the first electrode film 5.

In Example 10, a sputtering target containing materials described in Table 1 was used for the piezoelectric thin film 3. In Example 11, as described in Table 1, a sputtering target further containing 0.11 at % Ba and 6.5 at % Ta was used. In Example 12, as described in Table 1, a sputtering target further containing 0.11 at % Ba, 6.5 at % Ta, and 0.35 at % Mn was used. Here, the elements were contained in such a manner that the total content of the elements in the entire piezoelectric thin film containing the elements was 100 at %. Thereafter, the thin-film piezoelectric element 100 was produced as in Example 1.

(Evaluation of Thin-Film Piezoelectric Element)

For the thin-film piezoelectric element 100 in each of Examples 1 to 12 and Comparative Examples 1 to 6, the amount of displacement under a voltage of 20 V was measured with a laser Doppler vibrometer (manufactured by GRAPHTEC corporation). The dielectric loss tangent of each thin-film piezoelectric element 100 was measured with an impedance analyzer 4294A (manufactured by Agilent Technologies, Inc.) at a measurement voltage of 0.5 mV, a measurement frequency of 100 to 10000 Hz. Next, a leakage current density was evaluated with a ferroelectric evaluation system TF-1000 (manufactured by aixACCT) at a measurement voltage of ±20 V and a measurement frequency of 100 Hz. The resulting measurement values are described in Table 1.

The values of Tan $\delta_{100}$ at a measurement frequency of 100 Hz and the ratio of Tan $\delta_{10000}$ at a measurement frequency of 10 KHz to Tan $\delta_{100}$ at a measurement frequency of 100 Hz (Tan $\delta_{10000}$/Tan $\delta_{100}$) are described in Table 1. The values of Tan $\delta_{100}$ in Comparative Examples 1 to 6 were as high as 0.071 or more. In contrast, the values of Tan $\delta_{100}$ in Examples 1 to 12 were 0.059 or less. Furthermore, in many examples, the values of Tan $\delta_{100}$ were 0.05 or less. Similarly, the values of Tan $\delta_{10000}$/Tan $\delta_{100}$ in Comparative Examples 1 to 6 were as high as 1.64 or more. In contrast, the values of Tan $\delta_{10000}$/Tan $\delta_{100}$ in Examples 1 to 12 were 1.4 or less.

As described above, in the thin-film piezoelectric element including the piezoelectric thin film which has an alkali niobate-based perovskite structure represented by the composition formula $(K_{1-w-x}Na_wSr_x)_m(Nb_{1-y}Zr_y)O_3$ (0.95≤m<1.05, and 0.6≤(m·x/y)≤0.8) and which is preferentially oriented to (001), it is possible to achieve sufficiently low values of Tan $\delta_{100}$ and Tan $\delta_{10000}$/Tan $\delta_{100}$.

When Tan $\delta_{100}$ is 0.05 or less, the thin-film piezoelectric element does not generate heat during operation. When Tan $\delta_{10000}$/Tan $\delta_{100}$ is 1.5 or less, the thin-film piezoelectric element does not generate heat during operation even in a high frequency region.

Figure 7:
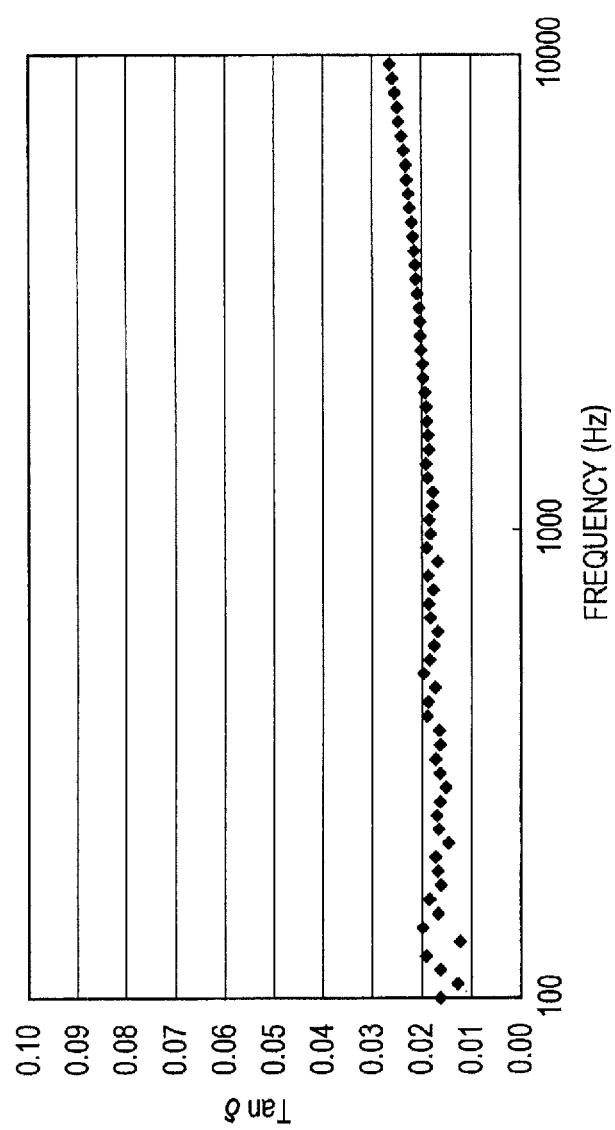
FIG. 7 is a correlation graph illustrating the relationship between Tan δ of a lead-free piezoelectric thin film according to the present invention and the measurement frequency.

FIG. 7 is a correlation graph illustrating the relationship between Tan δ of a lead-free piezoelectric thin film in Example 12 and the measurement frequency. This demonstrates that Tan δ of the lead-free piezoelectric thin film of the present invention is low in the entire measured frequency region, compared with FIG. 1, which is a graph illustrating the relationship between Tan δ of a conventional lead-free piezoelectric thin film and the measurement frequency.

Figure 8:
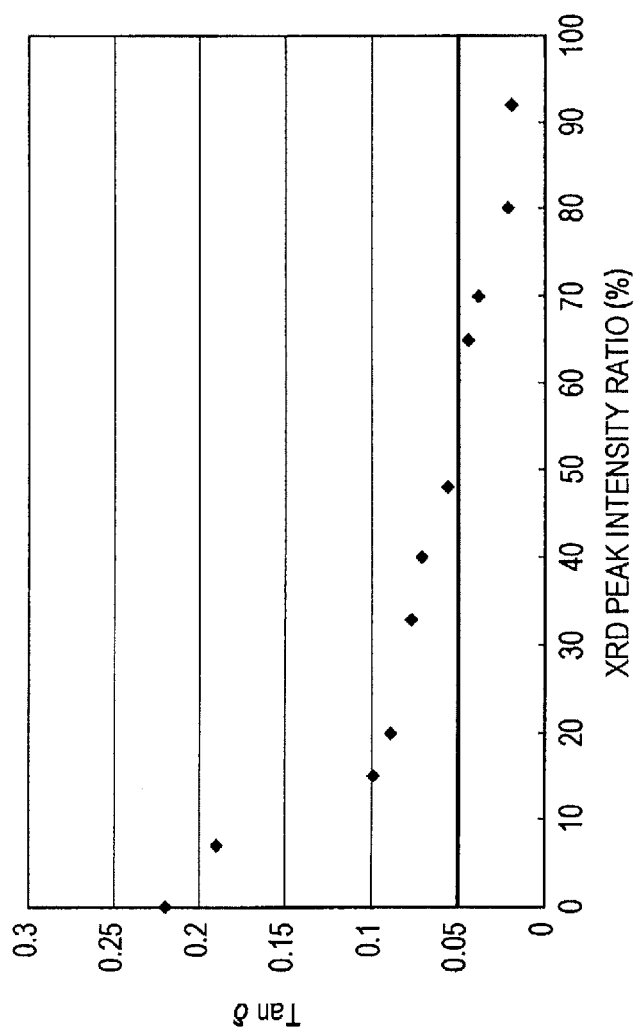
FIG. 8 is a graph illustrating the relationship between the degrees of (001) orientation and Tan δ of a lead-free piezoelectric thin film.

FIG. 8 illustrates the relationship between the degrees of (001) orientation and Tan δ:Tan $δ_{100}$ at a measurement frequency of 100 Hz of the piezoelectric thin films 3 having various compositions produced in Examples 2, 3, 11, and 12 and Comparative Examples 1, 3, 5, and 6. This figure demonstrates that when the piezoelectric thin film 3 is preferentially oriented to (001), i.e., when the XRD peak intensity ratio exceeds 50%, Tan $δ_{100}$ is reduced to 0.05 or less.

Among piezoelectric thin films having an alkali niobate-based perovskite structure that satisfies the foregoing composition range, i.e., 0.95≤m<1.05, and 0.6≤(m·x/y) 0.8, in the case where the Na/(Na+K) ratio is 0.5 or more and 0.75 or less, the leakage current and piezoelectric properties were particularly satisfactory.

With respect to the leakage current density, in Example 5, in which the Na/(Na+K) ratio was less than 0.5, the leakage current density was a value of the order of $10^{-6}$ A/cm² or more. In contrast, in each of Examples 6 to 8, in which the Na/(Na+K) ratios were 0.5 or more and 0.75 or less, the leakage current density was a value of the order of $10^{-7}$ A/cm². In each of Examples 1 to 4 and 9, in which the Na/(Na+K) ratio exceeded 0.75, the amount of displacement was slightly small. In each of Examples 6 to 8, in which the Na/(Na+K) ratio was 0.5 or more and 0.75 or less, the amount of displacement exceeded 10 μm.

As described in Table 1, the amounts of displacement of the thin-film piezoelectric elements in Comparative Examples 1 to 6 were 4.2 to 6.6 μm. In contrast, the amounts of displacement in Examples 1 to 12 were 6.5 to 11.2 μm. With respect to the piezoelectric properties of the thin-film piezoelectric element, in the element shape in these examples, an amount of displacement of 5 μm or more is practical. The amount of displacement is preferably 10 μm or more.

In each of Comparative Examples 4 to 6, while the amount of displacement was 5 μm or more, the leakage current density was high. The reason for this may be that since the value of m was outside the preferred range or (Sr/Zr) was outside the preferred range, the lattice defects in the piezoelectric thin film 3 were increased. In Comparative Example 3, in which the piezoelectric thin film 3 was preferentially oriented to a plane other than (001), the leakage current density was satisfactory. However, as described above, the dielectric loss was not reduced, and sufficient piezoelectric properties were not provided.

As described above, with respect to the thin-film piezoelectric element 100 in each of Examples 10 to 12, the thin-film piezoelectric element 100 including the intermediate film 4 between the first electrode film 5 and the piezoelectric thin film 3 and being produced with the sputtering target, to which Ba, Ta, and Mn were added, for the piezoelectric thin film, the amount of displacement of 11.0 to 11.2 μm, and Tan δ:Tan $δ_{100}$ was 0.018 to 0.024 at a measurement frequency of 100 Hz, which were satisfactory. Furthermore, the leakage current density was a value of the order of $10^{-8}$ A/cm². As is clear from the results, the arrangement of the intermediate film 4 improves the orientation of the piezoelectric thin film 3 to improve the piezoelectric properties, thereby increasing the amount of displacement. Furthermore, the addition of Ba, Ta, and Mn to the piezoelectric thin film having an alkali niobate-based perovskite structure provides the low-leakage-current-density thin-film piezoelectric element.

The thin-film piezoelectric element according to the present invention includes the alkali niobate-based piezoelectric thin film having the perovskite structure that falls within a predetermined composition range and that is preferentially oriented to (001); and the pair of electrode films that sandwich the piezoelectric thin film. In the case where the piezoelectric thin film having low dielectric loss and a large amount of displacement is used as a piezoelectric thin film for a piezoelectric actuator, it is possible to achieve a sufficient amount of displacement without heat generation during operation.

In the case where the piezoelectric thin film having low dielectric loss and a large amount of displacement is used as a piezoelectric thin film for a piezoelectric sensor, it is possible to achieve sufficient detection sensitivity without heat generation during operation.

In the case where the piezoelectric thin film having low dielectric loss and a large amount of displacement is used as a thin-film piezoelectric element for a head assembly of a hard disk drive, it is possible to achieve sufficient accessibility without heat generation during operation.

In the case where the piezoelectric thin film having low dielectric loss and a large amount of displacement is used as a thin-film piezoelectric element for a piezoelectric actuator of an ink jet printer head, it is possible to provide a high-safety ink jet printer apparatus without heat generation during printing.

TABLE 1

$(K_{1-w-x}Na_wSr_x)_m(Nb_{1-y}Zr_y)O_3 + α$

| | Target composition | | | | | | | | | | | | | |
|---|---|---|---|---|---|---|---|---|---|---|---|---|---|---|
| | K (1−w−x) | Na (w) | Sr (x) | Nb (1−y) | Zr (y) | Additive element | m | Sr/Zr (m·x/y) | Na/(Na+K) | KNN preferred orientation | Intermediate film | Tan δ 100 | Tan δ ratio | Leakage current density (A/cm2) | Amount of displacement (μm) |
| Example 1 | 0.17 | 0.76 | 0.07 | 0.90 | 0.10 | none | 0.96 | 0.67 | 0.82 | (001) | none | 0.059 | 1.4 | 5.7E−06 | 6.5 |
| Example 2 | 0.17 | 0.76 | 0.07 | 0.90 | 0.10 | none | 1.00 | 0.70 | 0.82 | (001) | none | 0.055 | 1.39 | 5.9E−06 | 6.8 |
| Example 3 | 0.17 | 0.76 | 0.07 | 0.90 | 0.10 | none | 1.04 | 0.73 | 0.82 | (001) | none | 0.047 | 1.39 | 7.7E−06 | 7.1 |
| Example 4 | 0.18 | 0.76 | 0.06 | 0.92 | 0.08 | none | 1.04 | 0.78 | 0.81 | (001) | none | 0.037 | 1.39 | 5.4E−06 | 9.8 |
| Example 5 | 0.54 | 0.40 | 0.06 | 0.92 | 0.08 | none | 1.04 | 0.78 | 0.43 | (001) | none | 0.033 | 1.38 | 4.5E−06 | 8.8 |
| Example 6 | 0.44 | 0.50 | 0.06 | 0.92 | 0.08 | none | 1.04 | 0.78 | 0.53 | (001) | none | 0.033 | 1.38 | 4.5E−07 | 10.1 |
| Example 7 | 0.34 | 0.60 | 0.06 | 0.92 | 0.08 | none | 1.04 | 0.78 | 0.64 | (001) | none | 0.032 | 1.37 | 2.7E−07 | 10.5 |
| Example 8 | 0.24 | 0.70 | 0.06 | 0.92 | 0.08 | none | 1.04 | 0.78 | 0.74 | (001) | none | 0.029 | 1.37 | 2.3E−07 | 10.8 |
| Example 9 | 0.19 | 0.75 | 0.06 | 0.92 | 0.08 | none | 1.04 | 0.78 | 0.80 | (001) | none | 0.025 | 1.37 | 8.0E−08 | 7.1 |
| Example 10 | 0.34 | 0.60 | 0.06 | 0.92 | 0.08 | none | 1.04 | 0.78 | 0.64 | (001) | arranged | 0.024 | 1.36 | 7.1E−08 | 11 |
| Example 11 | 0.34 | 0.60 | 0.06 | 0.92 | 0.08 | Ba, Ta | 1.04 | 0.78 | 0.64 | (001) | arranged | 0.022 | 1.35 | 6.7E−08 | 11.1 |
| Example 12 | 0.34 | 0.60 | 0.06 | 0.92 | 0.08 | Ba, Ta, Mn | 1.04 | 0.78 | 0.64 | (001) | arranged | 0.018 | 1.36 | 6.2E−08 | 11.2 |

TABLE 1-continued $(K_{1-w-x}Na_wSr_x)_m(Nb_{1-y}Zr_y)O_3 + \alpha$

| | Target composition | | | | | | | | | | | | | | |
|---|---|---|---|---|---|---|---|---|---|---|---|---|---|---|---|
| | K (1−w−x) | Na (w) | Sr (x) | Nb (1−y) | Zr (y) | Additive element | m | Sr/Zr (m·x/y) | Na/(Na+K) | KNN preferred orientation | Intermediate film | Tan δ 100 | Tan δ ratio | Leakage current density (A/cm2) | Amount of displacement (μm) |
| Comparative Example 1 | 0.53 | 0.40 | 0.07 | 0.90 | 0.10 | none | 0.84 | 0.59 | 0.43 | (001) | none | 0.22 | 2.3 | 5.5E−02 | 4.2 |
| Comparative Example 2 | 0.53 | 0.40 | 0.07 | 0.90 | 0.10 | none | 0.90 | 0.63 | 0.43 | (001) | none | 0.23 | 2.24 | 5.0E−02 | 4.4 |
| Comparative Example 3 | 0.53 | 0.40 | 0.07 | 0.90 | 0.10 | none | 0.96 | 0.67 | 0.43 | (110) | none | 0.1 | 1.65 | 8.8E−06 | 4.4 |
| Comparative Example 4 | 0.50 | 0.38 | 0.07 | 0.90 | 0.10 | none | 1.06 | 0.74 | 0.43 | (001) | none | 0.4 | 3.15 | 5.4E−02 | 5.6 |
| Comparative Example 5 | 0.50 | 0.38 | 0.07 | 0.92 | 0.08 | none | 1.04 | 0.91 | 0.43 | (001) | none | 0.076 | 1.67 | 4.5E−02 | 6.6 |
| Comparative Example 6 | 0.18 | 0.76 | 0.06 | 0.90 | 0.10 | none | 0.96 | 0.58 | 0.81 | (001) | none | 0.071 | 1.64 | 4.5E−02 | 6.6 |

Tan δ ratio = Tan δ 10000/Tan δ 100

What is claimed is:

1. A thin-film piezoelectric element comprising:
 a piezoelectric thin film; and a pair of electrode films that sandwich the piezoelectric thin film,
 wherein the piezoelectric thin film has an alkali niobate-based perovskite structure represented by the composition formula $(K_{1-w-x}Na_wSr_x)_m(Nb_{1-y}Zr_y)O_3$ and is preferentially oriented to (001),
 wherein
 $0.95 \leq m < 1.05$, and $0.6 \leq (m \cdot x/y) \leq 0.8$.

2. The thin-film piezoelectric element according to claim 1, wherein in the piezoelectric thin film, a Na (sodium)/(Na+K (potassium)) ratio is 0.5 or more and 0.75 or less.

3. The thin-film piezoelectric element according to claim 1, further comprising a strontium ruthenate thin film provided between the piezoelectric thin film and at least one of the pair of electrode films.

4. The thin-film piezoelectric element according to claim 1, wherein m=0.96 and (m·x/y)=0.67.

5. The thin-film piezoelectric element according to claim 1, wherein m=1.00 and (m·x/y)=0.70.

6. The thin-film piezoelectric element according to claim 1, wherein m=1.04 and (m·x/y)=0.73.

7. The thin-film piezoelectric element according to claim 1, wherein m=1.04 and (m·x/y)=0.78.

8. A thin-film piezoelectric actuator comprising the thin-film piezoelectric element according to claim 1.

9. A thin-film piezoelectric sensor comprising the thin-film piezoelectric element according to claim 1.

10. A hard disk drive comprising the thin-film piezoelectric actuator according to claim 8.

11. An ink jet printer apparatus comprising the thin-film piezoelectric actuator according to claim 8.

* * * * *